US011226343B2

(12) United States Patent
Lasalle et al.

(10) Patent No.: US 11,226,343 B2
(45) Date of Patent: Jan. 18, 2022

(54) METHODS AND KITS FOR DIAGNOSING POSTOPERATIVE PULMONARY INFECTIONS IN PATIENTS WHO UNDERWENT SURGERY

(71) Applicants: LUNGINNOV, Lille (FR); INSERM (INSTITUTE NATIONAL DE LA SANTÉ ET DE LA RECHERCHE MÉDICALE), Paris (FR); UNIVERSITE DE LILLE, Lille (FR); INSTITUT PASTEUR DE LILLE, Lille (FR); CENTRE NATIONAL DE LA RECHERCHE SCIENTIFIQUE—CNRS -, Paris (FR)

(72) Inventors: Philippe Lasalle, Lille (FR); Sidney Chocron, Besancon (FR); Nathalie De Freitas Caires, Wasquehal (FR)

(73) Assignees: BIOTHELIS, Hellemmes Lille (FR); INSERM (INSTITUT NATIONAL DE LA SANTE ET DE LE RECHERCHE MEDICAL), Paris (FR); INSTITUT PASTEUR DE LILLE, Lille (FR); CENTRE NATIONAL DE LA RECHERCHE SCIENTIFIQUE—CNRS—, Paris (FR); UNIVERSITE DE LILLE, Lille (FR)

( * ) Notice: Subject to any disclaimer, the term of this patent is extended or adjusted under 35 U.S.C. 154(b) by 495 days.

(21) Appl. No.: 16/092,027

(22) PCT Filed: Apr. 7, 2017

(86) PCT No.: PCT/EP2017/058387
§ 371 (c)(1),
(2) Date: Oct. 8, 2018

(87) PCT Pub. No.: WO2017/174786
PCT Pub. Date: Oct. 12, 2017

(65) Prior Publication Data
US 2019/0162736 A1   May 30, 2019

(51) Int. Cl.
*G01N 33/68* (2006.01)
*G01N 33/74* (2006.01)

(52) U.S. Cl.
CPC ......... *G01N 33/6893* (2013.01); *G01N 33/74* (2013.01); *G01N 2800/12* (2013.01); *G01N 2800/26* (2013.01)

(58) Field of Classification Search
CPC ........... G01N 2800/26; G01N 2800/12; G01N 33/6893; G01N 33/74
See application file for complete search history.

(56) References Cited

U.S. PATENT DOCUMENTS

| 6,309,888 B1 * | 10/2001 | Holvoet | G01N 33/6893 435/7.1 |
| 2003/0109420 A1 * | 6/2003 | Valkirs | G01N 33/6887 435/7.1 |

FOREIGN PATENT DOCUMENTS

| WO | 2010/064223 A2 | 6/2010 |
| WO | 2012/098219 A1 | 7/2012 |
| WO | WO-2016046634 A1 * | 3/2016 ............ A61M 1/73 |

OTHER PUBLICATIONS

El Halim et al. "Serum endocan role in diagnosis and prognosis of ventilator associated pneumonia", Egyptian Journal of Chest Diseases and Tuberculosis (2015) 64, 865-869, http://dx.doi.org/10.1016/j.ejcdt.2015.05.015 (Year: 2015).*
Perrotti et al. "Relevance of Endothelial Cell-Specific Molecule 1 (Endocan) Plasma Levels for Predicting Pulmonary Infection after Cardiac Surgery in Chronic Kidney Disease Patients: The Endolung Pilot Study" Cardiorenal Med 2018;8:1-8, DOI: 10.1159/000479337 (Year: 2018).*
Perotti et al. "Is Endocan a Diagnostic Marker for Pneumonia After Cardiac Surgery? The ENDOLUNG Study" Ann Thorac Surg 2018;105:535-41, http://dx.doi.org/10.1016/j.athoracsur.2017.07.031 (Year: 2018).*
ClinicalTrials.gov, Identifier: NCT02542423 "Endocan Predictive Value in Postcardiac Surgery Acute Respiratory Failure", including Key Record Dates and History of Changes, 14 pages total, Posted Sep. 7, 2015, retrieved from https://clinicaltrials.gov/ct2/show/NCT02542423 (Year: 2015).*
Madhivathanan et al. "Perioperative kinetics of endocan in patients undergoing cardiac surgery with and without cardiopulmonary bypass" Cytokine 83 (2016) 8-12, Available online Mar. 19, 2016, http://dx.doi.org/10.1016/j.cyto.2016.03.006 (Year: 2016).*
Stoppelkamp et al. "Identification of Predictive Early Biomarkers for Sterile-SIRS after Cardiovascular Surgery" PLoS ONE 10(8):e0135527. doi:10.1371/journal.pone.0135527, pp. 1-20 (Year: 2015).*
Li et al. "Detection on Dynamic Changes of Endothelial Cell Specific Molecule-1 in Acute Rejection After Renal Transplantation" Urology vol. 80, Issue 3, Sep. 2012, pp. 738.e1-738.e8, http://dx.doi.org/10.1016/j.urology.2012.03.019 (Year: 2012).*
Mihajlovic et al. "Endocan is useful biomarker of survival and severity in sepsis" Microvascular Research 93 (2014) 92-97 (Year: 2014).*
Mangat et al. "High Endocan Levels Predict the Need for Ventilatory Support Among Patients With Severe Sepsis" Chest 2015;148(4_MeetingAbstracts):345A. doi:10.1378/chest.2271136 (Year: 2015).*
Jebali et al. "Assessment of the accuracy of procalcitonin to diagnose postoperative infection after cardiac surgery", Anesthesiology Aug. 2007;107(2):232-8. doi: 10.1097/01.anes.0000271871.07395.ad. (Year: 2007).*

(Continued)

*Primary Examiner* — Christine Foster
(74) *Attorney, Agent, or Firm* — W&C IP

(57) ABSTRACT

The present invention relates to methods and kits for diagnosing a postoperative pulmonary infection in a patient who underwent surgery. More particularly, the present invention relates to a method for diagnosing a postoperative pulmonary infection in a patient who underwent surgery, comprising a step consisting of measuring the concentration of endocan in a blood sample obtained from said patient, at a time point comprised between 3 h and 30 h after surgery.

11 Claims, 1 Drawing Sheet

(56) References Cited

OTHER PUBLICATIONS

Kao et al., "Plasma endothelial cell-specific molecule-1 (ESM-1) in management of community-acquired pneumonia", Clinical Chemistry and Laboratory Medicine: Journal of the Forum of the European Societies of Clinical Chemistry, Mar. 1, 2014, pp. 445-451, vol. 52, No. 3.
Aouifi et al., "Usefulness of procalcitonin for diagnosis of infection in cardiac surgical patients", Critical Care Medicine, Sep. 1, 2000, pp. 3171-3176, vol. 28, No. 9, Lippincott Williams & Wilkins, US.
Palud et al., "Evaluation of endothelial biomarkers as predictors of organ failures in septic shock patients", Cytokine, Mar. 17, 2015, pp. 213-218, vol. 73, No. 2.
De Freitas et al., "Etude de la degradation d'endocan par les neutrophiles et implicaiton dans le sepsis", Web, Dec. 19, 2008.

* cited by examiner

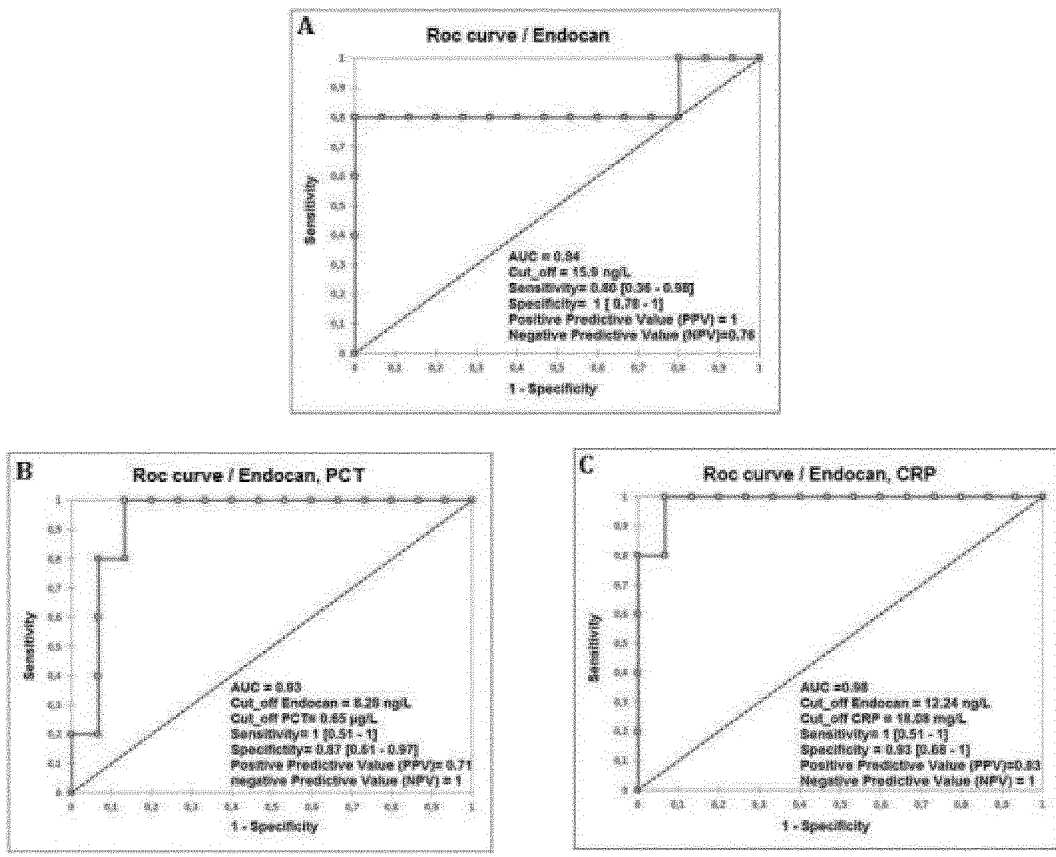

METHODS AND KITS FOR DIAGNOSING POSTOPERATIVE PULMONARY INFECTIONS IN PATIENTS WHO UNDERWENT SURGERY

FIELD OF THE INVENTION

The present invention relates to methods and kits for the early diagnosis of a postoperative pulmonary infection in a patient who underwent surgery.

BACKGROUND OF THE INVENTION

Postoperative pulmonary infections after cardiac surgery have an incidence between 5.7% and 21.6% [1] and lead to death from 8.1% to 31.9% of cases [2-4]. Its diagnosis is often lately achieved because of several confounding elements due to perioperative inflammation and the lack of diagnostic performances of current infection markers in the immediate postoperative period.

Endocan (Endothelial cell specific molecule 1 or ESM-1) is a proteoglycan that can be detected in human blood and is produced and secreted by endothelial cells, mainly from lung, and more accessorily from kidney [5, 6]. The selective expression by lung endothelium is governed by a proximal region of its promoter (Tsai et al, 2001). Endocan can take part in molecular interactions with wide range of biologically active moieties, which are essential for regulation of biological processes such as cell adhesion, migration, proliferation and neovascularization [7]. Endocan binds to the Leukocyte Function Associated Antigen-1 (LFA-1), inhibits LFA-1 interactions with endothelial Inter Cellular Adhesion Molecule-1 (ICAM-1) and thus is able to modulate leukocyte migration from blood flow into tissues [8,9]. The synthesis and secretion of endocan are upregulated by pro-inflammatory cytokines like TNFα or Interleukine-1b and lipopolysaccharides [5].

Endocan has been showing to provide good results in the early detection of acute lung injury after major trauma or in septic shock patients [10, 11]. Kao et al. reported in a recent study that endocan is reliable in evaluating the severity of community-acquired pneumonia [12]. Guzel et al. also found a correlation between plasmatic endocan levels and thromboembolism [13]. Other biomarkers have been shown to have an interest in detecting infection. From one hand, procalcitonin (PCT) has already been tested in cardiac surgery but its role remains controversial. Some authors clearly describe its correlation with the onset of postoperative infections [14] and also ventilator associated pneumonia [15]. Other authors, like Chakravarthy et al, found no significant serum PCT levels difference between patients with or without bacterial infections after cardiac surgery [16]. From another hand, C-reactive protein (CRP), another marker widely used, seems to be less specific, and peak later than PCT to detect infections [17, 18].

There is thus a need for an early diagnosis for postoperative pulmonary infections. Said diagnosis has to be easy to perform, with reliable results. Moreover, said diagnosis has to be performed early after surgery, so as to quickly treat the concerned patients. This avoids waiting too long, even a few days, for obtaining the diagnosis.

SUMMARY OF THE INVENTION

The inventors have now identified that the level of endocan in blood, particularly in plasma, in the hours following surgery, is highly correlated to the presence of a postoperative pulmonary infection. Indeed, the measure of endocan concentration at 6 h after surgery is highly predictive of a postoperative pulmonary infection.

Thus, the present invention relates to a method for diagnosing a postoperative pulmonary infection in a patient who underwent surgery, comprising a step of measuring the concentration of endocan in a blood sample obtained from said patient, at a time point comprised between 3 h and 30 h after surgery.

DETAILED DESCRIPTION OF THE INVENTION

The inventors show that blood endocan level represents a tool for the early diagnosis of postoperative pulmonary infection in patients who underwent surgery.

Accordingly, the present invention relates to a method for diagnosing a postoperative pulmonary infection in a patient who underwent surgery, comprising a step of measuring the concentration of endocan in a blood sample obtained from said patient, at a time point comprised between 3 h and 30 h after surgery, preferably between 5 h and 25 h after surgery. Said method is reliable, and shows a very good sensitivity and a very good specificity, as explained in the example.

As used herein the term "patient who underwent surgery" refers to a patient who underwent any kind of surgery. Particularly, it may be cardiac surgery, brain surgery, abdominal surgery or orthopedic surgery.

As used herein the term "postoperative pulmonary infection" means a pulmonary infection which occurs after surgery. Postoperative pulmonary infections are health-care associated pneumonia (HCAP) (or nosocomial pneumonia), and are at high risk of multidrug-resistant pathogens. Comorbidities are also an issue with such infections. Postoperative pulmonary infections are a different class from community-acquired pneumonia (CAP), which occurs outside of healthcare facilities.

Postoperative pulmonary infections are usually caused by a bacterial infection, rather than a virus. They are associated with cough, phlegm, shortness of breath, chest pain, temperature above 38° C., and pulse rate above 100 a minute. Up to half of people may have asymptomatic chest signs after surgery, and up to a quarter develop symptomatic disease. The main risk factor is the type of surgery, with higher risks associated with surgery to the chest, abdomen, and head and neck compared with other operations. Other risk factors include age over 50 years, chronic obstructive pulmonary disease (COPD), smoking, hypoalbuminaemia, and being functionally dependent.

Preferably, the postoperative pulmonary infection diagnosed according to the invention is a nosocomial pneumonia. Preferably, it is a bacterial pneumonia, preferably due to a bacteria chosen from various gram-negative bacilli and *Staphylococcus aureus*. Among the various gram-negative bacilli, one can quote *Haemophilus* spp., such as *H. influenzae*, *Pseudomonas aeruginosa*, *Klebsiella pneumonia* and *Enterobacter* spp. Preferably, the nosocomial pneumonia is a viral pneumonia, which may be due to influenza and respiratory syncytial virus or to cytomegalovirus.

As used herein the term "endocan" or "ESM-1" has its general meaning in the art and refers to the endothelial cell specific molecule-1 that is a 50-kDa dermatan sulfate proteoglycan expressed by endothelial cells in lung and kidney (Lassalle P, Molet S, Janin A, et al: ESM-1 is a novel human endothelial cell-specific molecule expressed in lung and regulated by cytokines. J Biol Chem 1996; 271:20458-

20464) and can be detected in human blood (Bechard D, Meignin V, Scherpereel A, et al: Characterization of the secreted form of endothelial-cell-specific molecule 1 by specific monoclonal antibodies. J Vasc Res 2000; 37:417-425; Bechard D, Gentina T, Delehedde M, et al: Endocan is a novel chondroitin sulfate/dermatan sulfate proteoglycan that promotes hepatocyte growth factor/scatter factor mitogenic activity. J Biol Chem 2001; 276:48341-48349).

As used herein the term "blood sample" refers to a whole blood, serum, or plasma sample.

Once the blood sample from the patient is prepared, the concentration of ESM-1 may be measured by any known method in the art. For example, the concentration of ESM-1 may be measured by using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, high performance liquid chromatography (HPLC), size exclusion chromatography, solid-phase affinity, etc.

In a particular embodiment, such methods comprise contacting the blood sample with a binding partner capable of selectively interacting with ESM-1 present in the blood sample.

The binding partner may be generally an antibody that may be polyclonal or monoclonal, preferably monoclonal. Polyclonal antibodies directed against ESM-1 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against ESM-1 can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g. U.S. Pat. No. 4,946,778) can be adapted to produce anti-ESM-1, single chain antibodies. Antibodies useful in practicing the present invention also include anti-ESM-1 fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to ESM-1. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

Anti-ESM-1 monoclonal antibodies are commercially available from Lunginnov (Lille, France). For example, anti-human endocan/ESM-1 antibody MEPO8 detects the N-terminus of human endocan (Bechard et al. (2000) J. Vasc. Res. 37:417-425; Grigoriu et al. (2006) Clin. Cancer Res. 12:4575-4582; Maurage et al. (2009) Exp. Neurol. 68:836-844; Leroy et al. (2010) Histopathology 56:180-187; Sarrazin et al. (2010) J. Canc. Sci. Ther. 2:47-52). Anti-human endocan/ESM-1 antibody clone MEP19 detects the C-terminus of human endocan (Bechard et al. (2000) J. Vasc. Res. 37:417-425; Grigoriu et al. (2006) Clin. Cancer Res. 12:4575-4582; Maurage et al. (2009) Exp. Neurol. 68:836-844; Leroy et al. (2010) Histopathology 56:180-187; Sarrazin et al. (2010a) J. Canc. Sci. Ther. 2:47-52; and Sarrazin et al. (2010b) Glycobiology 20:1380-1388).

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as *E. coli* Thioredoxin A, that are selected from combinatorial libraries by two hybrid methods (Colas et al., 1996).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labeled", with regard to the antibody, is intended to encompass direct labeling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labeling of the probe or antibody by reactivity with a detectable substance. An antibody or aptamer of the invention may be labeled with a radioactive molecule by any method known in the art. For example radioactive molecules include but are not limited radioactive atom for scintigraphic studies such as I123, I124, In111, Re186, Re188.

The aforementioned assays generally involve the bounding of the binding partner (ie. Antibody or aptamer) in a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with a set of antibodies against ESM-1. A blood sample containing or suspected of containing ESM-1 is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Typically an ELISA kit is commercially available from Lunginnov (Lille, France): EndoMark H1 ® (ELISA Kit to detect human endocan). Other ELISA methods are described in: Bechard et al. (2000) J. Vasc. Res. 37:417-425; Grigoriu et al. (2006) Clin. Cancer Res. 12:4575-4582; Leroy et al. (2010) Histopathology 56:180-187; Sarrazin et al. (2006) BBA Reviews 1765:25-37; Sarrazin et al. (2010a) J. Canc. Sci. Ther. 2:47-52; Scherpereel et al. (2003) Cancer Res. 63:6084-6089; Scherpereel et al. (2006) Crit. Care Med. 34(2):532-537.

Measuring the concentration of ESM-1 (with or without immunoassay-based methods) may also include separation of the proteins: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, ESM-1 may be identified based on the known "separation profile" e. g., retention time, for that protein and measured using standard techniques. Alternatively, the separated proteins may be detected and measured by, for example, a mass spectrometer.

The method of the invention is for diagnosing a postoperative pulmonary infection in a patient who underwent surgery, by measuring the concentration of endocan in a blood sample of said patient, at a time point comprised between 3 h and 30 h after surgery, preferably 5 h and 25 h after surgery. Preferably, the time point is comprised between 5 h and 12 h after surgery, preferably a cardiac surgery.

The method further shows a very good sensitivity and a very good specificity, as shown in the example.

The method of the invention may comprise a step of comparing the concentration of endocan (ESM-1) with a predetermined threshold value. Said comparison is indicative whether said patient is at risk of being afflicted by a postoperative pulmonary infection. For example, the predetermined threshold value represents the concentration measured in average in healthy patients, namely patients that will not develop a postoperative pulmonary infection. Typically a higher concentration than the predetermined threshold value determined in healthy patients predicts a postoperative pulmonary infection, at a time point comprised between 3 h and 30 h after surgery, preferably 5 h and 25 h after surgery, preferably between 5 h and 12 h after surgery, preferably 6 h after surgery.

Preferably, the step of measuring the concentration of endocan in a blood sample is performed at a time point comprised between 3 h and 30 h after surgery, preferably 5 h and 25 h after surgery, preferably between 5 h and 12 h after surgery, preferably 6 h after surgery, and if said concentration is greater than 8 ng/ml, preferably greater than 10 ng/ml, preferably greater than 12 ng/ml, preferably greater than 14 ng/ml, preferably greater than 15, preferably greater than 15.9 ng/ml, preferably greater than 16 ng/ml, then said patient is at risk of being afflicted by a postoperative pulmonary infection.

Preferably, said threshold value is correlated with at least 80% sensitivity and at least 80% specificity.

Preferably, the step of measuring the concentration of endocan in a blood sample is performed at a time point of 6 h after surgery, and if said concentration is greater than 15.9 ng/ml, then said patient is at risk of being afflicted by a postoperative pulmonary infection.

Preferably, the step of measuring the concentration of endocan in a blood sample is performed at a time point of 6 h after cardiac surgery, and if said concentration is greater than 15.9 ng/ml, then said patient is at risk of being afflicted by a postoperative pulmonary infection. Indeed, said threshold value is correlated with a 80% sensitivity and a 100% specificity.

Preferably, the method of the invention further comprises a step of measuring the concentration of procalcitonin, in a blood sample obtained from said patient, at a time point comprised between 3 h and 30 h after surgery, preferably 5 h and 25 h after surgery, preferably between 5 h and 12 h after surgery, preferably 6 h after surgery. Preferably, said step of measuring the concentration of procalcitonin in a blood sample is performed at a time point of 6 h after surgery, preferably cardiac surgery, and if said concentration is greater than 0.6 µg/l, preferably greater than 0.65 µg/l and the concentration of endocan is greater than 8 ng/ml, preferably greater than 8.28 ng/ml, then said patient is at risk of being afflicted by a postoperative pulmonary infection.

The method of the invention may also further comprise a step of measuring the concentration of C reactive protein, in a blood sample obtained from said patient, at a time point comprised between 3 h and 30 h after surgery, preferably 5 h and 25 h after surgery, preferably between 5 h and 12 h after surgery, preferably 6 h after surgery. Preferably, said step of measuring the concentration of C reactive protein in a blood sample is performed at a time point of 6 h after surgery, preferably cardiac surgery, and if said concentration is greater than 18 mg/l, preferably greater than 18.08 mg/l and the concentration of endocan is greater than 12 ng/ml, preferably greater than 12.24 ng/ml, then said patient is at risk of being afflicted by a postoperative pulmonary infection.

The method of the invention may also further comprise a preliminary step of measuring the concentration of endocan in a blood sample of said patient, before surgery. Preferably, said measure is performed at a time point of at most 12 h before surgery, preferably at induction of general anesthesia of said surgery.

In such a case, said preliminary step may comprise comparing the concentration of ESM-1 with a predetermined threshold value. Said comparison is indicative whether said patient is at risk of being afflicted by a postoperative pulmonary infection. For example, the predetermined threshold value represents the concentration measured in average in healthy patients, namely patients that will not develop a postoperative pulmonary infection. Typically a lower concentration than the predetermined threshold value determined in healthy patients predicts a postoperative pulmonary infection.

Preferably, said preliminary step is performed at a time point at most 12 h before surgery, preferably at induction of general anesthesia of said surgery, and if said concentration is lower than 3 ng/ml, then said patient is at risk of being afflicted by a postoperative pulmonary infection.

Preferably, the method for diagnosing a postoperative pulmonary infection in a patient who underwent surgery according of the invention, comprises the following steps:

a preliminary step of measuring the concentration of endocan in a blood sample of said patient, before surgery, preferably at induction of general anesthesia of said surgery, a subsequent step of measuring the concentration of endocan in a blood sample of said patient, at a time point comprised between 3 h and 30 h after surgery, preferably 5 h and 25 h after surgery, and if the concentration obtained in the preliminary step is lower than a threshold value, preferably 3 ng/ml, and if the concentration obtained in the subsequent step is greater than 8 ng/ml, preferably greater than 15, preferably greater than 15.9 ng/ml, then said patient is at risk of being afflicted by a postoperative pulmonary infection.

The method of the invention may be thus useful for early classifying patients afflicted by a postoperative pulmonary infection, and then may be used to quickly choose the accurate treatment. For example, patients at risk of developing a postoperative pulmonary infection may receive a more intensive treatment and attention compared to patient with a weak risk. Such method may thus help the physician to make a choice on a therapeutic treatment which can accordingly consist in administering accurate drugs to the patients. Costs of the treatments may therefore be adapted to the patients after surgery.

A further object of the invention relates to the use of ESM-1 as a marker of a postoperative pulmonary infection in a patient who underwent surgery.

Yet another object of the invention relates to a kit for diagnosing a postoperative pulmonary infection, comprising means for measuring the concentration of ESM-1. The kit may include an antibody, or a set of antibodies as above described. In a particular embodiment, the antibody or set of antibodies are labelled as above described. The kit may also contain other suitably packaged reagents and materials needed for the particular detection protocol, including solid-phase matrices, if applicable, and standards. The kit may also contain means for the detection of other markers of postoperative pulmonary infection, such as C reactive protein (CRP) or procalcitonin (PCT).

Finally, the present invention also relates to a method for treating a postoperative pulmonary infection in a patient who underwent surgery, comprising the steps of:

a) diagnosing a postoperative pulmonary infection in a patient who underwent surgery, comprising a step of measuring the concentration of endocan in a blood sample obtained from said patient, at a time point comprised between 3 h and 30 h after surgery, preferably 5 h and 25 h after surgery, preferably between 5 h and 12 h after surgery, preferably 6 h after surgery; and b) if said patient is at risk for being afflicted by a postoperative pulmonary infection, then treating said patient with an antibiotic or an antiviral.

The antibiotic treatment is highly preferred, because bacterial infection is the most common cause of postoperative pulmonary infection. Thus, among the possible antibiotic, one may quote penicillins such as penicillin and amoxicillin; cephalosporins such as cephalexin, cefoxitin, cefotaxime, cefepime and ceftobiprole; macrolides such as erythromycin, clarithromycin and azithromycin; fluoroquinolones such as ciprofloxacin, levofloxacin and ofloxacin; sulfonamides such as co-trimazole and trimethoprim; tetracyclines such as tetracycline and doxycycline; and aminoglycosides such as gentamicin and tobramycin.

Among the possible antiviral treatment, one may quote acyclovir and ganciclovir.

The invention will be further illustrated by the following FIGURES and examples. However, these examples and FIGURES should not be interpreted in any way as limiting the scope of the present invention.

FIGURES

FIG. 1. Receiver Operating Characteristic (ROC) curves of biomarker plasma levels at 6 hours after the end of surgery.
A: endocan alone,
B: association endocan-PCT, and
C: association endocan-CRP.

Example 1: Interest of Plasma Endocan Level in Predicting Pulmonary Infection after Cardiac Surgery This pilot study aimed to evaluate the interest of endocan plasmatic level in predicting pulmonary infection after cardiac surgery.

Patients and Methods

In a previous prospective cohort study (NGAL study [19]), 166 adult patients with preoperative chronic renal failure who underwent cardiac surgery with or without the use of cardiopulmonary bypass were enrolled. Chronic renal failure was defined as a Crockroft creatinine clearance<60 ml/min. Patients undergoing emergency operations, patients with ongoing inflammatory, infectious or oncologic pathologies, pregnant women, adults under legal protection and people denying their consent were excluded. Blood samples were taken on EDTA containers at 5 time points: at induction of general anesthesia (baseline), and 6, 12 and 24 hours after the end of surgery. Blood samples were centrifuged at 2250±250 rpm for 13±2 minutes at room temperature (18-25° Celsius), and plasma was aliquoted in 0.5 mL tubes (Eppendorf, Le Pecq, France) and frozen at −20° Celsius for later analysis. The NGAL study was approved by the local ethics committee (CPP EST II, registered under the number 10/544) and was registered on the ClinicalTrials.gov database under the number NCT01227122. All participants provided written informed consent where they gave the authorization to conserve and use their serum for other research purposes.

Nosocomial pneumonia was diagnosed on the presence of all the following criteria: fever >38.8° C., rales, leukocytosis (>11,000/cm$^3$), detection of new or progressive lung infiltrate(s) not explained otherwise, and purulent respiratory secretion yielding growth of relevant pathogen. A positive culture of blood, pleural fluid, or bronchoalveolar lavage was regarded as additional proof of nosocomial pneumonia.

In the NGAL study, five patients presented a postoperative pulmonary infection. These patients were randomly matched (⅓) to 15 patients of the same study who had an uneventful outcome. There was no statistical difference between age, sex, or renal function between the 2 groups.

Endocan, PCT, and CRP were measured on plasma collection. Endocan was measured using the Lunginnov ELISA kit named EndoMark® H1, which is based on immunoenzymatic assay (Lunginnov SAS, Lille, France). Measuring range is from 0.625 to 5 ng/mL. During the study period, the between-assay imprecision was 12%, based on a quality control sample targeted at 3.5 ng/mL. PCT and CRP were measured on Roche Cobas®8000 analysers (Roche Diagnostics, Meylan, France), using PCT immunoassay kit (BRAHMS ThermoFisher Scientific, Asnieres-sur-Seine, France) and CRP Gen3 immunoturbidimétric kit (Roche Diagnostics, Meylan, France), respectively. HUPC laboratory complied with all recommended quality controls (internal and external quality controls) for all routine tested biomarkers during the study period.

The inventors analyzed the ability to detect early postoperative infectious complications of each biomarker and their associations.

Statistical Analysis

Continuous variables are presented as means±standard deviation, categorical variables as number (percentage). Quantitative variables were compared by Student t-test and U-Mann Whitney test, according to their distribution. The associations of different biomarkers were compared by performing ROC curves. The reliability of the analysis was tested by calculating the area underneath the curve, the cut-off value, the specificity, the sensibility and the predictive value. The validity of our single biomarkers or their associations as adequate diagnostic predictors was assessed by the Youden index. All statistical analysis were performed using SAS version 9.2 (SAS Institute Inc. Cary. N.C., USA).

Results

Endocan Kinetic

Average was 78+/−10 years among the 5 patients with pulmonary infection, and 77+/−7 among those with uneventful outcome (p=0.49). between patients who presented postoperative infection, and those with uneventful course, there was no significant difference in BMI (respectively: 31+/−10 versus 24+/−3, p=0.12), Diabete mellitus (respectively: 2 patients (40%) versus 1 patient (7%), p=0.14), left ventricular ejection fraction (respectively: 60+/−12 versus 57+/−14, p=0.55), pre-operative creatinine clearance (respectively: 44+/−13 versus 47+/−9 mL/min/1.73 m², p=0.67). conversely all patients (100%) with pulmonary infection, and 6 patients (40%) with uneventful outcome were males (p=0.04).

The kinetic of endocan blood levels shows a progressive increase over time in patients with pulmonary infections but also in patients with uneventful outcome (Table 1).

TABLE 1

Preoperative, 6 h, 12 h, 24 h endocan, PCT and CRP plasma levels according to subsequent pulmonary infection

| Biomarker | Timing | Pulmonary infection | Mean ± SD | P value |
|---|---|---|---|---|
| Endocan | Preoperative | No | 3.07 ± 2.37 | 0.69 |
| | | Yes | 2.21 ± 1.47 | |
| | 6 h | No | 6.44 ± 3.16 | 0.03 |
| | | Yes | 24.16 ± 15.64 | |
| | 12 h | No | 9.79 ± 7.18 | 0.07 |
| | | Yes | 25.27 ± 14.35 | |
| | 24 h | No | 13.17 ± 6.68 | 0.63 |
| | | Yes | 15.14 ± 15.29 | |
| PCT | Preoperative | No | 0.05 ± 0.03 | 0.26 |
| | | Yes | 0.11 ± 0.12 | |
| | 6 h | No | 0.90 ± 1.70 | 0.11 |
| | | Yes | 4.32 ± 7.03 | |
| | 12 h | No | 1.32 ± 2.43 | 0.22 |
| | | Yes | 6.13 ± 9.65 | |
| | 24 h | No | 2.04 ± 3.15 | 0.6 |
| | | Yes | 6.49 ± 11.08 | |
| CRP | Preoperative | No | 3.38 ± 4.91 | 0.19 |
| | | Yes | 16.81 ± 29.41 | |
| | 6 h | No | 15.18 ± 9.39 | 0.01 |
| | | Yes | 48.54 ± 41.29 | |
| | 12 h | No | 51.83 ± 18.09 | 0.03 |
| | | Yes | 102.8 ± 65.21 | |
| | 24 h | No | 137.91 ± 51.03 | 0.1 |
| | | Yes | 197.76 ± 89.29 | |

PCT: Procalcitonin;
CRP: C-reactive protein

Diagnostic Performances of Biomarkers:

Patients with pulmonary infections had significantly higher levels of endocan at 6 h postoperatively than patients with uneventful outcome (p=0.03) (Table 1). For these patients, when the diagnosis of pneumonia was established 53+/−20 hours after the operation, and the antibiotic treatment started only after an average of 62+/−27 hours. The ROC curve for endocan at 6 hours showed the best diagnostic performance for the detection of pulmonary infections, with an AUC at 0.84, and a 80% sensitivity and a 100% specificity for a cut-off value of 15.9 ng/mL (FIG. 1A). PCT levels showed no relevant differences between infected and not infected patients. CRP levels at 6 and 12 hours correlated with postoperative pulmonary infections with a p value of 0.01 and 0.03 respectively.

Diagnostic Performances of Combined Biomarkers:

The association of biomarkers showed that endocan and PCT taken together present a sensitivity of 100% and a specificity of 87% at 6 hours, with cut-off values at 8.28 ng/mL for endocan and 0.65 ng/mL for PCT (FIG. 1B). Endocan and CRP association had a sensitivity of 100% and a specificity of 93% at 6 hours, with cut-off values at 12.24 ng/mL for endocan and 18.08 mg/L for CRP (FIG. 1C).

REFERENCES

Throughout this application, various references describe the state of the art to which this invention pertains. The disclosures of these references are hereby incorporated by reference into the present disclosure.

1. Michalopoulos A, Geroulanos S, Rosmarakis E S, Falagas M E. Frequency, characteristics, and predictors of microbiologically documented nosocomial infections after cardiac surgery. Eur J Cardiothorac Surg 2006; 29:456-60.
2. Melsen W G, Rovers M M, Groenwold R H, Bergmans D C, Camus C, Bauer T T, Hanisch E W, Klarin B, Koeman M, Krueger W A, Lacherade J C, Lorente L, Memish Z A, Morrow L E, Nardi G, van Nieuwenhoven C A, O'Keefe G E, Nakos G, Scannapieco F A, Seguin P, Staudiger T, Topeli A, Ferrer M, Bonten M J: Attributable mortality of ventilator-associated pneumonia: a meta-analysis of individual patient data from randomized prevention studies. Lancet Infect Dis 2013, 13:665-671.
3. Nguile-Makao M, Zahar J R, Francais A, Tabah A, Garrouste-Orgeas M, Allaouchiche B, Goldgran-Toledano D' Azoulay E, Adrie C, Jamali S, Souweine B, Timsit J F: Attributable mortality of ventilator-associated pneumonia: respective impact of main characteristics at ICU admission and VAP onset using conditional logistic regression and multi-state models. Intensive Care Med 2010, 36:781-789.
4. Cunnion K M, Weber D J, Broadhead W E, Hanson L C, Pieper C F, Rutala W A: Risk factors for nosocomial 5. Lassalle P, Molet S, Janin A, Heyden J V, Tavernier J, Fiers W, et al. ESM-1 is a novel human endothelial cell-specific molecule expressed in lung and regulated by cytokines. J Biol Chem 1996; 271(34):20458-64.
6. Sarrazin S, Adam E, Lyon M, Depontieu F, Motte V, Landolfi C, et al. Endocan or endothelial cell specific molecule-1 (ESM-1): a potential novel endothelial cell marker and a new target for cancer therapy. Biochim Biophys Acta 2006; 1765(1):25-37.
7. Kali A, Shetty K S: Endocan: A novel circulating proteoglycan. Indian J Pharmacol 2014; 46(6):579-583.
8. Béchard D, Scherpereel A, Hammad H, Gentina T, Tsicopoulos A, Aumercier M, et al. Human endothelial-cell specific molecule-1 binds directly to the integrin CD11a/CD18(LFA-1) and blocks binding to intercellular adhesion molecule-1. J Immunol 2001; 167(6):3099-106.
9. Tissier S, Lancel S, Marechal X, Mordon S, Depontieu F, Scherpereel A, et al. Calpain inhibitors improve myocardial dysfunction and inflammation induced by endotoxin in rats. Shock 2004; 21(4):352-7.
10. Palud A, Parmentier-Decrucq E, Pastre J, De Freitas Caires N, Lassalle P, Mathieu D: Evaluation of endothelial biomarkers as predictors of organ failures in septic shock patients. Cytokine 2015; 73(2):213-218.
11. Mikkelsen M E, Shah C V, Scherpereel A, Lanken P N, Las salle P, Bellamy S L, Localio A R, Albelda S M, Meyer N J, Christie J D. Lower serum endocan levels are associated with the development of acute lung injury after major trauma. J Crit Care 2012; 27(5): 522.e11-7
12. Kao S J, Chuang C Y, Tang C H, Lin C H, Bien M Y, Yu M C, Bai K J, Yang S F, Chien M H. Plasma endothelial cell-specific molecule-1 (ESM-1) in management of community-acquired pneumonia. Clin Chem Lab Med 2014; 52(3):445-51.
13. Güzel A, Duran L, Koksal N, Torun A C, Alaçam H, Ekiz B C, Murat N. Evaluation of serum endothelial cell specific molecule-1 (endocan) levels as a biomarker in patients with pulmonary thromboembolism. Blood Coagul Fibrinolysis 2014; 25(3):272-6
14. Jebali M A, Hausfater P, Abbes Z, Aouni Z, Riou B, Ferjani M. Assessment of the accuracy of procalcitonin to diagnose postoperative infection after cardiac surgery. Anesthesiology 2007; 107(2):232-8.
15. Jiao J, Wang M, Zhang J, Shen K, Liao X, Zhou X. Procalcitonin as a diagnostic marker of ventilator-associated pneumonia in cardiac surgery patients. Exp Ther Med 2015; 9(3):1051-1057.
16. Chakravarthy M, Kavaraganahalli D, Pargaonkar S, Hosur R, Harivelam C, Bharadwaj A, Raghunathan A. Elevated postoperative serum procalcitonin is not indicative of bacterial infection in cardiac surgical patients. Ann Card Anaesth 2015; 18(2):210-4.
17. Simon L, Gauvin F, Amre D K, Saint-Louis P, Lacroix J. Serum procalcitonin and C-reactive protein levels as markers of bacterial infection: a systematic review and meta-analysis. Clin Infect Dis. 2004; 39(2):206-17.
18. Dong Z, Jianxin Z, Haraguchi G, Arai H, Mitaka C. Procalcitonin for the differential diagnosis of infectious and non-infectious systemic inflammatory response syndrome after cardiac operation. Zhonghua Wei Zhong Bing Ji Jiu Yi Xue 2014; 26(7):478-9.
19. Perrotti A, Miltgen G, Chevet-Noel A, Durst C, Vernerey D, Bardonnet K, Davani S, Chocron S: Neutrophil gelatinase-associated lipocalin as early predictor of acute kidney injury after cardiac surgery in adults with chronic kidney failure. Ann Thorac Surg 2015; 99(3):864-9.
20. Meisner M, Rauschmayer C, Schmidt J, Feyrer R, Cesnjevar R, Bredle D, Tschaikowsky K. Early increase of procalcitonin after cardiovascular surgery in patients with postoperative complications. Intensive Care Med 2002; 28(8):1094-102.
21. Meisner M, Tschaikowsky K, Hutzler A, Schick C, Schüttler J. Postoperative plasma concentrations of procalcitonin after different types of surgery. Intensive Care Med 1998; 24(7):680-4.
22. Rothenburger M, Markewitz A, Lenz T, Kaulbach H G, Marohl K, Kuhlmann W D, Weinhold C. Detection of acute phase response and infection. The role of procalcitonin and C-reactive protein. Clin Chem Lab Med 1999; 37(3):275-9.
23. Shehabi Y, Seppelt I. Pro/Con debate: Is procalcitonin useful for guiding antibiotic decision making in critically ill patients? Crit Care 2008; 12(3):211.

The invention claimed is:

1. A method for diagnosing and treating a postoperative pulmonary infection in a patient who underwent surgery, comprising
measuring the concentration of endocan in a blood sample obtained from said patient, at a time point comprised between 3 h and 30 h after surgery;
comparing the concentration of endocan with a predetermined threshold value, and diagnosing said patient as being at risk of being afflicted by a postoperative pulmonary infection when the concentration of endocan is greater than said threshold value; and
administering an antibiotic or an antiviral to said patient diagnosed as being at risk of being afflicted by a postoperative pulmonary infection.

2. The method according to claim 1, wherein the time point is comprised between 5 h and 12 h after surgery.

3. The method according to claim 1, wherein the patient underwent cardiac surgery, brain surgery, abdominal surgery or orthopedic surgery.

4. The method according to claim 1, wherein the blood sample is a whole blood, serum, or plasma sample.

5. The method according to claim 1, wherein the postoperative pulmonary infection is a nosocomial pneumonia.

6. The method according to claim 1, wherein if said concentration of endocan is greater than 8 ng/ml, then said patient is at risk of being afflicted by a postoperative pulmonary infection.

7. The method according to claim 1, further comprising a step of measuring the concentration of procalcitonin, in a blood sample obtained from said patient, at a time point comprised between 3 h and 30 h after surgery.

8. The method according to claim 7, wherein the step of measuring the concentration of procalcitonin in a blood sample is performed at a time point of 6 h after surgery, and if said concentration of procalcitonin is greater than 0.6 µg/l, and the concentration of endocan is greater than 8 ng/ml, then said patient is at risk of being afflicted by a postoperative pulmonary infection.

9. The method according to claim 1, further comprising a step of measuring the concentration of C reactive protein, in a blood sample obtained from said patient, at a time point comprised between 3 h and 30 h after surgery.

10. The method according to claim 9, wherein the step of measuring the concentration of C reactive protein in a blood sample is performed at a time point of 6 h after surgery, and if said concentration of C reactive protein is greater than 18 mg/l, and the concentration of endocan is greater than 12 ng/ml, then said patient is at risk of being afflicted by a postoperative pulmonary infection.

11. The method according to claim 1, further comprising a preliminary step of measuring the concentration of endocan in a blood sample of said patient before surgery.

* * * * *